United States Patent [19]

Deckner et al.

[11] 4,452,989
[45] Jun. 5, 1984

[54] SUBSTANTIVE MOISTURIZING DERIVATIVES OF 2-PYRROLIDONE-5-CARBOXYLIC ACID AND COMPOSITIONS CONTAINING SAME

[75] Inventors: George E. Deckner, Westfield; Hedwig O'Grady, Holmdel; Albert Zofchak, Matawan, all of N.J.

[73] Assignee: Charles of the Ritz Group Ltd., New York, N.Y.

[21] Appl. No.: 384,137

[22] Filed: Jun. 1, 1982

[51] Int. Cl.$^3$ .......................................... C07D 207/28
[52] U.S. Cl. ................................ 548/537; 252/522 R; 424/63; 424/64; 424/69; 424/70; 424/358; 424/365; 548/534
[58] Field of Search ................ 548/537, 534

[56] References Cited

U.S. PATENT DOCUMENTS

| | | | |
|---|---|---|---|
| 2,890,979 | 6/1959 | Korner | 548/534 |
| 3,002,978 | 10/1961 | Bocher | 548/519 |
| 3,051,722 | 8/1962 | Biel | 548/537 X |
| 3,948,943 | 4/1976 | Eberhardt et al. | 548/537 |
| 3,952,011 | 4/1976 | Dazai et al. | 548/534 |

OTHER PUBLICATIONS

C.A., vol. 83 (1975), 28562x, Eberhardt et al.

Chem. Abstracts, vol. 87 (1977), 202159r, (Marini).
Chem. Abstracts, vol. 51 (1957), 17880d, (Angier et al.).
Chem. Abstracts (1961), 21094e, vol. 55, (Cocolas et al.).
Chem. Abstracts, vol. 65 (1966), 2199g, (Brunet et al.).

*Primary Examiner*—Joseph Paul Brust
*Attorney, Agent, or Firm*—Lawrence S. Levinson; Burton Rodney

[57] ABSTRACT

Derivatives of 2-pyrrolidone-5-carboxylic acid having excellent moisturizing properties are provided which have the structure

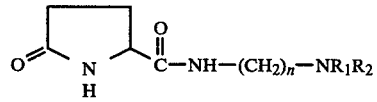

wherein $R_1$ and $R_2$ are the same or different and are lower alkyl and aralkyl and n is 1 to 8 and including cationic salts thereof such as the pyrrolidone carboxylic acid salt thereof. These compounds are useful as moisturizing agents.

Cosmetics, shampoos, hair conditioners and skin toners containing such compounds are also provided.

5 Claims, No Drawings

SUBSTANTIVE MOISTURIZING DERIVATIVES OF 2-PYRROLIDONE-5-CARBOXYLIC ACID AND COMPOSITIONS CONTAINING SAME

FIELD OF THE INVENTION

The present invention relates to derivatives of 2-pyrrolidone-5-carboxylic acid having unique moisturizing properties and to cosmetic, skin and hair treatment compositions containing same.

BACKGROUND OF THE INVENTION

2-Pyrrolidone-5-carboxylic acid and its sodium salt are generally known for their use as humectants for cosmetics, soaps, lotions including colognes, perfumes, hair preparations, detergent and dentifrices because of their moistening effect and non-irritancy to skin and eye mucosa as disclosed in AJIDEW A-100 and N-50 Spec. sheets, Ajinomoto Co., Inc.

DESCRIPTION OF THE INVENTION

In accordance with the present invention, novel derivatives of 2-pyrrolidone-5-carboxylic acid are provided which are excellent moisturizing agents for cosmetics, hair preparations such as shampoos and conditioners, skin toners and colognes and the like and have the following structure

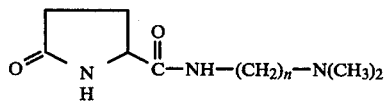

I wherein n is an integer of from 1 to 8 and preferably 2 to 5, and more preferably 3.

In addition, in accordance with the present invention, novel water-soluble substantive moisturizing cationic salts of derivatives of 2-pyrrolidone-5-carboxylic acid are provided which salts have the structure

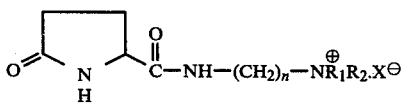

II wherein n is 1 to 8, preferably 2 to 5, $R_1$ and $R_2$ are the same or different and are lower alkyl or aralkyl, and each is preferably methyl or ethyl, and $X^\ominus$ represents a moisturizing cationic moiety such as 2-pyrrolidone-5-carboxylic acid, gluconic acid, lactic acid, citric acid, phosphoric acid, acetic acid, tartaric acid, hydrochloric acid, or sulfuric acid, and preferably 2-pyrrolidone-5-carboxylic acid.

The above salts are formed of cationic and anionic portions which both contribute to the moisturizing properties of the compounds; however, the salts are generally considered cationic in nature since they readily bind to skin and hair (which are anionic).

The salts may be formed by heating a mixture of the desired acid and parent compound (preferably employing stoichiometric amounts) at a temperature of 50° to 70° C. to form a clear liquid. The salts may also be formed in situ in a carrier composition such as a cosmetic.

In another aspect of the present invention, amine oxide, betaine and quaternary ammonium derivatives of the parent compound of the formula III are provided

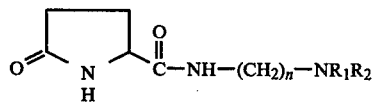

III wherein n is 1 to 8 and $R_1$ and $R_2$ are the same or different and are lower alkyl or aralkyl.

The amine oxide derivative in accordance with the invention has the structure

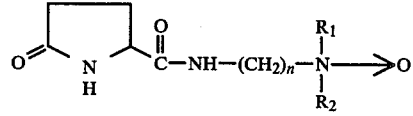

IV wherein n is 1 to 8 $R_1$ and $R_2$ are the same or different and are lower alkyl or aralkyl, and are formed by the reaction of hydrogen peroxide and the parent compound of formula III. These derivatives have weak cationic properties and therefore are more compatible in shampoos than the more cationic salts.

The betaine derivatives in accordance with the invention have the structure

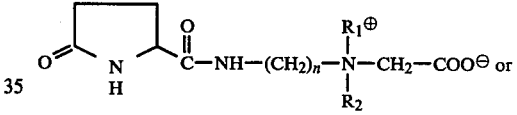

VA

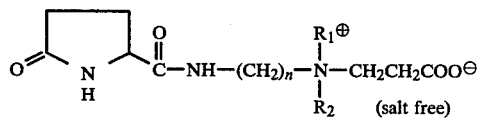

VB wherein n is 1 to 8, and $R_1$ and $R_2$ are the same or different and are lower alkyl or aralkyl. Compounds of formula VA are formed by the reaction of methyl acrylate or acrylic acid and the parent compound of formula III. Compounds of formula VB are formed by the reaction of sodium monochloroacetate and the parent compound of formula III.

The formula VB betaines are salt-free amphoteric compounds and therefore are compatible with anionic systems such as shampoos and are less substantive than the cationic compounds, that is the active component of the betaine does not tend to build-up on hair as much as if it were in the form of a cationic compound salt thereof.

The quaternary ammonium chloride salts in accordance with the present invention have the structure

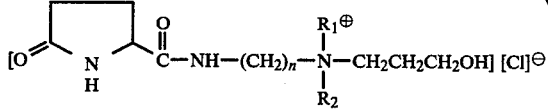

VI wherein n is 1 to 8 and $R_1$ and $R_2$ are the same or different and are lower alkyl or aralkyl and are formed by the reaction of epichlorohydrin and the parent compound of formula III.

Still further in accordance with the present invention, an emulsifier is provided which is comprised of a compound of the structure

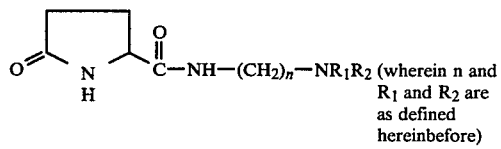

VII (wherein n and $R_1$ and $R_2$ are as defined hereinbefore)

neutralized with a fatty acid containing from 10 to 30 carbons, such as stearic acid, lauric acid, myristic acid, oleic acid or behenic acid. The mixture of the formulate VII compound and the fatty acid in a 1:1 molar ratio forms an excellent oil-in-water emulsifier, especially useful in cosmetic and skin preparations.

The compounds of formula I, and the parent compound of formula III or VIII are prepared by reacting 2-pyrrolidone-5-carboxylic acid, that is

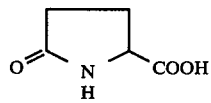

A with an excess of amine of the structure $$NH_2-(CH_2)_n-NR_1R_2 \qquad IX$$

of within the range of from about 125° to about 180° C. After from about 8 to about 10 hours, the amine IX is distilled off to leave the compound of Formula I or III or VIII. The formula I compound (where n is 3) will comprise a hot syrupy material which on cooling becomes a friable tacky water-soluble solid.

In further aspects of the present invention, there are also provided cosmetics, such as face powder, lipstick, rouge, mascara and nail cream, skin preparations, such as skin creams, hair preparations, such as shampoos and conditioners, colognes and skin-toners, soaps, bath oils and the like which contain any one or more of the various moisturizers set out above having the formula I, II, III, IV, V, VI, VII and/or VIII, and/or emulsifiers comprising a compound of formula VII where $R_1$ and $R_2$ are each preferably methyl or ethyl and n is 2 to 4, together with a fatty acid as described above.

The moisturizing compounds of the invention have been found to provide improved moisturization and conditioning properties as compared to 2-pyrrolidone-5-carboxylic acid in cosmetics and hair preparation products such as hair conditioners and shampoos.

The following Examples represent preferred embodiments of the present invention.

EXAMPLE 1

N-[3-(Dimethylamino)propyl]-5-oxo-2-pyrrolidinecarboxamide

129 Grams of 2-pyrrolidone-5-carboxylic acid were slowly added to 133 g of dimethylaminopropylamine with mixing. This mixture was then stirred and heated for 8-10 hours at 165° C. The excess amine was then distilled off having the title product in the form of an amber colored water-soluble solid.

EXAMPLE 2

N-[3-(Dimethylamino)propyl]-5-oxo-2-pyrrolidinecarboxamide, 2-pyrrolidone-5-carboxylate salt 129 Grams of 2-pyrrolidone-5-carboxylic acid were added to 214 grams of the Example 1 compound and 343 grams of deionized water. The resulting mixture was heated with stirring to 70° C. and mixed until clear. The pH of the final solution was between 6.0-6.5.

The pH of the final solution can be adjusted with 2-pyrrolidone-5-carboxylic acid or the Example 1 compound.

EXAMPLE 3

N-[3-(Diethylamino)ethyl]-5-oxo-2-pyrrolidinecarboxamide

129 Grams (1 mole) of 2-pyrrolidone-5-carboxylic acid are slowly added to 128 g (1.1 moles) of diethylaminoethylamine with mixing. This mixture is then stirred and heated for 8-10 hours at 165° C. The excess amine is then distilled off leaving the title product.

EXAMPLE 4

N-[3-(Diethylamino)ethyl]-5-oxo-2-pyrrolidinecarboxamide, 2-pyrrolidone-5-carboxylate salt 129 Grams of 2-pyrrolidone-5-carboxylic acid are added to 228 grams of the Example 3 compound along with 357 grams of deionized water. The resulting mixture is stirred and heated at 70° C. until clear. The pH of the final solution is between 6.0-6.5.

The pH of the final mixture can be adjusted to pH 6.0-6.5 with 2-pyrrolidone-5-carboxylic acid or the Example 3 compound.

EXAMPLE 5

N-[3-(Dipropylamino)butyl]-5-oxo-2-pyrrolidinecarboxamide

129 Grams (1 mole) of 2-pyrrolidone-5-carboxylic acid are slowly added to 185 g (1.1 moles) of dipropylaminobutylamine with mixing. This mixture is then stirred and heated for 8-10 hours at 165° C. The excess amine is then distilled off leaving the title product.

EXAMPLE 6

N-[3-(Dipropylamino)butyl]-5-oxo-]-2-pyrrolidinecarboxamide, citric acid salt

64 Grams of citric acid are added to 284 grams of the Example 5 compound with 348 grams of deionized water. The resulting mixture is heated with stirring to 70° C. until clear. The pH of the final solution is between 6.0-6.5.

The pH of the final mixture can be adjusted to pH 6.0-6.5 with the Example 5 compound or citric acid.

EXAMPLE 7

Amine oxide of N-[3-(Dimethylamino)propyl]-5-oxo-2-pyrrolidinecarboxamide

214 Grams of the Example 1 compound are dissolved in 100 grams of deionized water. To this mixture is slowly added 50 g of 35% hydrogen peroxide. This mixture is stirred for 8-10 hours at 60°-70° C. to form the title compound. Free amine is 1.5% maximum and free hydrogen peroxide 200 ppm maximum.

EXAMPLE 8

Betaine of
N-[3-(Dimethylamino)propyl]-5-oxo-2-pyrrolidinecarboxamide

116 Grams of sodium monochloroacetate are slowly added to 246 grams of Example 1 compound in the presence of 4 grams of 20 grams of sodium hydroxide (pH was kept between 7-9 during reaction). This mixture is stirred at 70°-80° C. for 12-15 hours to form the title compound.

EXAMPLE 9

Quaternary ammonium salt of
N-[3-(Dimethylamino)propyl]-5-oxo-2-pyrrolidinecarboxamide To 235 grams of the Example 1 compound are slowly added 93 grams of epichlorohydrin. This mixture is stirred at 70°-80° C. for 6-10 hours to form the title salt.

EXAMPLE 10

Emulsifier composition of
N-[3-(Dimethylamino)propyl]-5-oxo-2-pyrrolidinecarboxamide and stearic acid An emulsifier composition of the following formulation was prepared as described below.

| Ingredient | Grams |
| --- | --- |
| Deionized water | 81.40 |
| N—[3-(Dimethylamino)propyl]-5-oxo-2-pyrrolidine carboxamide (50% solution) | 2.00 |
| Carbowax 400 (PEG8) | 3.00 |
| Methyl paraben | 0.20 |
| Tegin 515 (glyceryl monostearate 40% mono) | 1.00 |
| Stearic acid | 3.00 |
| Acetulan (acetylated lanolin alcohol) | 4.00 |
| Purcellin oil (cetearyl octanoate) | 4.00 |
| Propyl paraben | 0.10 |
| Cetyl alcohol | 1.00 |
| Glydant (55% solution dimethyl dimethoyl hydantoin) | 0.30 |

The Carbowax 400 (polyethylene glycol 8) and methyl paraben were added to a 50% aqueous solution of N-[3-(dimethylamino)propyl]-5-oxo-2-pyrrolidine carboxamide and the mixture was heated with propeller mixing to 70° to 75° C. to form a first mix.

The glyceryl monostearate, stearic acid, acetylated lanolin alcohol, ceturyl octanoate, propyl paraben and cetyl alcohol were heated to 70°-75° C. with propeller mixing to form a second mix.

The second mix was then added to the first mix using propeller mixing. The mix was then cooled to 60° C. and then mixed via sweep mixing. Thereafter, the dimethyl dimethoyl hydantoin was added at 50° C. and the mix was cooled to 30° C. to form the emulsifier composition of the invention.

EXAMPLE 11

Cosmetic Formulation with
N-[3-(Dimethylamino)propyl]-5-oxo-2-pyrrolidinecarboxamide A cosmetic formulation having the following composition is prepared as described below.

| Ingredient | Grams |
| --- | --- |
| Deionized water | 76.00 |
| Glycerin | 3.00 |
| 2-Pyrrolidone-5-carboxylic acid (PCA) | 0.60 |
| N—[3-(Dimethylamino)propyl]-5-oxo-2-pyrrolidine carboxamide (50% soln) | 2.00 |
| Methyl paraben | 0.20 |
| Ceraphyl 368 (octyl palmitate) | 5.00 |
| Silicone 225 (dimethicone) | 2.00 |
| Tween 60 (polysorbate 60) | 3.00 |
| Propyl paraben | 0.10 |
| Tegin 515 (glyceryl monostearate 40% mono) | 2.00 |
| Promulgen D (cetearyl alcohol + ceteareth 20) | 5.50 |
| Deionized water | 0.50 |
| Dowicil 200 (Quaternium 15) | 0.10 |

Glycerin, 2-pyrrolidone-5-carboxylic acid, N-[3-(dimethylamino)propyl]-5-oxo-2-pyrrolidine carboxamide (50% aqueous solution) and methyl paraben were heated together to 70° to 75° C. with propeller mixing to form a first mix.

Octyl palmitate, dimethicone, polysorbate 60, propyl paraben, glyceryl monostearate and Promulgen D (ceturyl alcohol and Cetearth 20) were heated together to 70° to 75° C. with propeller mixing to form a second mix.

The second mix was then added to the first mix with propeller mixing and the mixture was then cooled to 60° C. while sweep mixing. Thereafter, aqueous Dowicil 20 (Quaternium 15) was added at 50° C. and the mixture was cooled to 30° C. to form the cosmetic of the invention.

EXAMPLE 12

Shampoo Formulation Containing
N-[3-(Dimethylamino)propyl]-5-oxo-2-pyrrolidinecarboxamide, 2-pyrrolidone-5-carboxylic acid salt A shampoo having the following composition was prepared as described below.

| Ingredient | Grams |
| --- | --- |
| Deionized water | 33.00 |
| Standapol ES2 (25% sodium laureth 2-sulfate) | 50.00 |
| Glydant (55% solution dimethyl dimethoyl hydantoin) | 0.30 |
| Standapol AB 45% (45% lauryl betaine) | 13.00 |
| Perfume oil | 0.50 |
| Triton X102 (octoxyonol 13) | 1.00 |
| Methyl paraben | 0.10 |
| FDC Yellow 6 (.1% solution) | 0.05 |
| FDC Red 4 (.1% solution) | 0.05 |
| 85% Phosphoric acid | (qs to pH 6.0) |
| N—[3-(Dimethylamino)propyl]-5-oxo-2-pyrrolidine carboxamide (50% solution) | 2.00 |

A first mix was formed by sweep mixing deionized water, Standapol ES2, Glydant and Standapol AB 45% while heating to 60°-65° C. The first mix was cooled to 50° C. and then perfume oil, Triton X102, Tegin, and the FD and C colors were added to the first mix with sweep mixing to form a second mix. The pH of the second mix was adjusted to 6.0 with phosphoric acid, at 50° C., and then the N-[3-(dimethylamino)propyl]-5-oxo-2-pyrrolidine carboxamide solution was added at 50° C. and the mix was cooled to 30° C. to form the shampoo formulation of the invention.

EXAMPLE 13

Hair Conditioner Containing N-[3-(Dimethylamino)propyl]-5-oxo-2-pyrrolidinecarboxamide, amine oxide A hair conditioner having the following composition is prepared as described below.

| Ingredient | Grams |
| --- | --- |
| Deionized water | 90.45 |
| Genamin DSAC (Quaternium 5) | 2.00 |
| Potassium chloride | 0.15 |
| N—[3-(Dimethylamino)propyl]-5-oxo-2-pyrrolidine carboxamide, amine oxide (50% solution) | 2.00 |
| Methyl paraben | 0.20 |
| Propyl paraben | 0.10 |
| Hastacerin T-3 (Ceteareth 3) | 1.50 |
| Cetyl alcohol | 1.50 |
| Stearyl alcohol | 1.50 |
| Perfume oil | 0.10 |
| Triton X102 (octoxyonol 13, that is, polyoxyethylene (13) octyl phenyl ether) | 0.50 |

The Genamin DSAC, KCl, amine oxide, Tegin and water are mixed together and heated at 70°-75° C. with propeller mixing to form a first mix.

The Tegl, Hastacerin T-3, cetyl alcohol and stearyl alcohol are mixed together at 70°-75° C. with propeller mixing to form a second mix.

The second mix is added to the first mix with propeller mixing. The combined mix is subjected to sweep mixing at 50° C. and perfume oil and Triton X102 are added. The batch is then cooled to 30° C. to form the hair conditioner of the invention.

EXAMPLE 14

Skin Toner Containing N-[3-(Dimethylamino)propyl]-5-oxo-2-pyrrolidinecarboxamide, quaternary ammonium salt A skin toner having the following composition is prepared as described below.

| Ingredient | Grams |
| --- | --- |
| Deionized water | 82.80 |
| Allantoin | 0.10 |
| SDA 40 (95% specially denatured ethanol) | 10.00 |
| Methyl paraben | 0.10 |
| Carbowax 400 (PEG 8) | 3.00 |
| Triton X102 (Octoxyonol 13) | 0.50 |
| Perfume oil | 0.10 |
| Quaternary ammonium salt of N—[3-(dimethylamino)propyl]-5-oxo-2-pyrrolidinecarboxamide (Ex. 9) (50% solution) | 2.00 |
| Deionized water | 1.00 |
| Germall 115 (Imidazolidinyl urea) | 0.40 |

Denatured ethanol, Tegin and Carbowax 400 are added to aqueous allantoin with propeller mixing until a clear solution is obtained. Thereafter, the Triton X102 and perfume oil are added with mixing until a clear solution is obtained. The quaternary ammonium salt of Example 9 is then added with mixing until a clear solution are obtained. Finally, water and Germall 115 are added with mixing until a clear solution comprising the skin toner of the invention is obtained.

EXAMPLE 15

Cosmetic Containing Emulsifier Composition Containing N-[3-(Dimethylamino)propyl]-5-oxo-2-pyrrolidinecarboxamide and Behenic Acid A cosmetic formulation having the following composition is prepared as described below.

| Ingredient | Grams |
| --- | --- |
| Deionized water | 81.40 |
| N—[3-(Dimethylamino)propyl]-5-oxo-2-pyrrolidine carboxamide (50% soln) | 2.00 |
| Carbowax 400 (PEG 8) | 3.00 |
| Methyl paraben | 0.20 |
| Tegin 515 (glyceryl monostearate 40% mono) | 1.00 |
| Behenic acid | 3.00 |
| Acetulan (acetylated lanolin alcohol) | 4.00 |
| Purcellin oil (cetaryl octanoate) | 4.00 |
| Propyl paraben | 0.10 |
| Cetyl alcohol | 1.00 |
| Glydant (55% solution dimethyl dimethoyl hydantoin) | 0.30 |

The Carbowax 400 (polyethylene glycol 8) and methyl paraben are added to a 50% aqueous solution of N-[3-(dimethylamino)propyl]-5-oxo-2-pyrrolidine carboxamide and the mixture is heated with propeller mixing to 70° to 75° C. to form a first mix.

The glyceryl monostearate, behenic acid, acetylated lanolin alcohol, ceturyl octanoate, propyl paraben and cetyl alcohol are heated to 70°-75° C. with propeller mixing to form a second mix.

The second mix is then added to the first mix using propeller mixing. The mix is then cooled to 60° C. and then mixed via sweep mixing. Thereafter, the dimethyl dimethoyl hydantoin is added at 50° C. and the mix is cooled to 30° C. to form the cosmetic composition of the invention.

What is claimed is:

1. A moisturizing compound of the structure

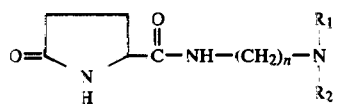

wherein n is 1 to 8 and $R_1$ and $R_2$ are the same or different and are lower alkyl or aralkyl, in the form of its amine oxide, betaine or quaternary ammonium salt having the structure

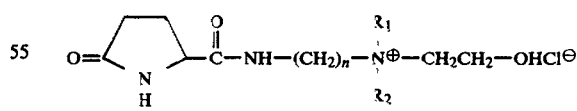

2. The compound as defined in claim 1 as the amine oxide having the structure

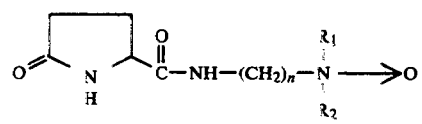

wherein n, $R_1$ and $R_2$ are as defined in claim 1.

3. The compound as defined in claim 1 as the betaine having the structure
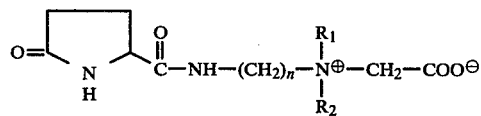
wherein n, R₁ and R₂ are as defined in claim 1.
4. The compound as defined in claim 1 as the betaine having the structure
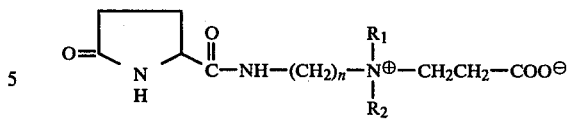
wherein n, R₁ and R₂ are as defined in claim 1.
5. The compound as defined in claim 1 as the quaternary salt having the structure
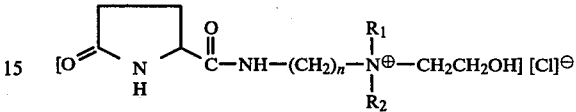
wherein n, R₁ and R₂ are as defined in claim 1.
* * * * *